United States Patent [19]

Song

[11] Patent Number: 4,724,094
[45] Date of Patent: Feb. 9, 1988

[54] FLUORESCENT MAGNETIC COMPOSITION AND METHOD OF MAKING AND USING SAME

[75] Inventor: Sei H. Song, Des Plaines, Ill.

[73] Assignee: Magnaflux Corporation, Chicago, Ill.

[21] Appl. No.: 699,030

[22] Filed: Feb. 7, 1985

[51] Int. Cl.$^4$ .............................................. C04B 35/00
[52] U.S. Cl. .............................. 252/62.52; 252/62.53; 252/62.54; 252/301.19; 252/301.34; 252/301.35
[58] Field of Search ............... 252/62.52, 62.53, 62.54, 252/301.19, 301.34, 301.35

[56] References Cited

U.S. PATENT DOCUMENTS

| 2,365,253 | 12/1944 | DeForest | 175/183 |
| 2,936,287 | 5/1960 | Kazenas | 252/62.52 |
| 3,404,093 | 10/1968 | Burrows | 252/62.52 |
| 3,485,758 | 12/1969 | Borucki et al. | 252/62.52 |
| 3,499,148 | 3/1970 | Nestler et al. | 252/62.52 |
| 3,573,979 | 4/1971 | Honjo | 252/62.54 |
| 3,597,356 | 8/1971 | Diperstein et al. | 252/62.52 |
| 3,609,532 | 9/1971 | VanKirk et al. | 324/38 |
| 4,338,566 | 7/1982 | Graham | 252/62.52 |
| 4,433,289 | 2/1984 | Mlot-Fijalkowski et al. | 252/62.52 |

FOREIGN PATENT DOCUMENTS

| 57-141547 | 9/1982 | Japan | 252/62.52 |
| 833267 | 4/1960 | United Kingdom | 252/62.52 |

Primary Examiner—John P. Sheehan
Attorney, Agent, or Firm—Curtis, Morris & Safford

[57] ABSTRACT

A method of preparing a fluorescent magnetic composition useful in non-destructing testing of metal work pieces. The method of the invention utilizes a plasticizer in order to effect a more complete encapsulation of fluorescent pigment and magnetic particle powder by film-forming resin. The invention also provides for the composition made by the inventive method, as well as for the method of using the composition in non-destructive testing of magnetizable work pieces.

14 Claims, No Drawings

FLUORESCENT MAGNETIC COMPOSITION AND METHOD OF MAKING AND USING SAME

FIELD OF THE INVENTION

The field of the present invention is non-destructive testing, and in a more particular vein fluorescent magnetic compositions useful in non-destructive testing of magnetizable work pieces, as well as the making and using of those fluorescent magnetic compositions.

BACKGROUND OF THE INVENTION

Methods for non-destructive testing of ferro-magnetic material (i.e. a "work piece") for flaws, defects and other discontinuities through the use of fluorescent magnetic particles have been described in a number of patents, for instance, U.S. Pat. Nos. 3,404,093 and 3,485,758. Conventional methods involve applying the fluorescent magnetic particles to the surface of the work piece, magnetizing the work piece and then inspecting the work piece under filtered ultraviolet light (also known as "black light") for characteristic patterns formed by particles which have migrated to the flaws. One of the advantages of using fluorescent magnetic particles for inspection purposes, as compared with magnetic particles having only visible coloration, is that there is a greatly increased contrast between the fluorescent magnetic particles and the background of the work piece, thereby easing the detection of flaws and the like.

Certain techniques for combining magnetic particles and fluorescent pigments are known in the art. See U.S. Pat. No. 2,365,253. One such technique involves incapsulation of pigment and magnetic particles to form a fluorescent pigment/magnetic particle composite. But conventional technology has certain drawbacks which significantly detract from its usefulness, especially in automatic testing applications.

Illustratively, consider the subject matter of U.S. Pat. No. 3,485,758, directed to a method of making fluorescent magnetic particles which involves encapulating a core including ferro-magnetic material and fluorescent pigment particles with a film-forming resin. Encapsulation is achieved by adding the resin to a mixture of pigment and ferro-magnetic material powders. Unfortunately, the patented method simply does not provide sufficient encapsulation, and thus a significant amount of pigment powder particles remain loose and unencapsulated. The presence of these loose pigment particles results in "background" fluorescence which interferes with the testing procedure ultimately performed on the work piece. The background fluorescence detracts from the contrast which is sought between fluorescent magnetic particles and the work piece background, thereby impeding the inspection of the surface of the work piece for flaws discontinuities, and other defects. Removal of the background fluorescence by screening of the material through a sieve has proven to be unsuccessful; due to the small size of the particles involved, they pass through the screen. Another method of removing background fluorescence by utilizing a magnetic field to separate out the magnetic particles has been found to be extremely inefficient and expensive.

A further disadvantage associated with conventional embodiments is that a lesser amount of pigment is encapsulated in each particle, the level of brightness of the desired fluorescence is lower and therefore difficulties from the lack of contrast are aggravated.

OBJECTS OF THE INVENTION

It is an object of the invention to provide a method of making a fluorescent magnetic composition which is readily detected on the surface of a ferro-magnetic work piece.

It is a further object of this invention to provide a method of making a fluorescent magnetic composition sufficiently detectable to be adaptable for the automated inspection of the surface of ferro-magnetic work pieces.

It is also an object of the invention to provide a method of making a fluorescent magnetic composition in which a more complete encapsulation of fluorescent pigment powder and magnetic particle powder is achieved.

It is an additional object of this invention to provide a method of making a fluorescent magnetic composition in which there is less unencapsulated loose fluorescent pigment powder and therefore less background fluorescence to detract from the testing of the ferro-magnetic work piece.

It is another object of this invention to provide a method of making a fluorescent magnetic composition in which there is a greater amount of fluorescent pigment powder encapsulated with the core-forming particles, thereby providing the resulting particles with a higher brightness level of fluorescence and therefore a higher degree of detectability.

It is still another object of this invention to provide a fluorescent magnetic composition which is made by the method of the invention, and is characterized by the aforementioned advantages.

It is yet another object of the invention to provide a method of using a fluorescent magnetic composition which is made by the method of the invention, and method of use is characterized by the aforementioned advantages.

These and other objects are met by the present invention.

STATEMENT AND ADVANTAGES OF THE INVENTION

In one of the aspects, the present invention is directed to a method of making a fluorescent magnetic composition which comprises admixing a magnetic powder with a fluorescent pigment powder to provide core particles in which the magnetic powder and pigment powder adhere to each other. The core particles are combined with a mixture of a volatile, water-miscible solvent, a plasticizer, water, and a water-precipitable film forming resin. Either the water or the film-forming resin is added as the last of the aforementioned components. This causes the resin to precipitate as an adherent coating over the core particles, thereby encapsulating them.

In another aspect, the invention is directed to a fluorescent magnetic composition which is manufactured by the method of admixing a magnetic powder with a fluorescent pigment powder to provide core particles in which the magnetic powder and pigment powder adhere to each other. The core particles are combined with a mixture of a volatile, water-miscible solvent, a plasticizer, water, and a water-precipitable film-forming resin, the water or the film-forming resin being added as the last of these components. The resin precipitates as an adherent coating over the core particles, thereby encapsulating them.

In still another aspect, the invention is directed to a method of using the fluorescent magnetic composition of the invention in the non-destructive testing of a magnetizable metal workpiece. This method comprises magnetizing the workpiece and then applying to it a suspension containing the fluorescent magnetic composition prepared in accordance with the inventive method. The work piece is then inspected under ultraviolet light for flaws indicated by the presence of clusters of magnetic particles on the work piece surface.

Numerous advantages accrue with the practice of the present invention. A greater amount of encapsulated pigment powder, and conversely a substantially decreased amount of unencapsulated powder, are obtained, which results in a decreased level of "background" fluorescence. Additionally, since more pigment powder is encapsulated, the brightness level of resulting fluorescence is higher, facilitating the detection of flaws or defects, if any, in the work piece on which the magnetic composition is ultimately utilized. Thus, it can be seen that the fluorescent magnetic composition provided by the inventive method is ideally suited for use in the examination of ferro-magnetic work pieces for defects or flaws.

In the following section the invention is described in greater detail to illustrate several of its embodiments.

DESCRIPTION OF CERTAIN PREFERRED EMBODIMENTS

A central feature of the present invention is the utilization of a plasticizer substance. The plasticizer ensures a high degree of encapsulation of the magnetic particle by the pigments and resin. It is the recognition of the ability of certain substances to act as plasticizers when included in the manufacturing process, thereby resulting in a more complete encapsulation of the core particles, which leads to solution of the prior problems stemming from the art's inability to detect fluorescent flaw indications readily and with certainty (due to unacceptably low contrast between fluorescent magnetic particles and the work piece background).

Any suitable ferro-magnetic (elsewhere herein, simply "magnetic" in accordance with conventional terminology) particles, for example, magnetic iron oxides, such as the magnetites, $Fe_3O_4$, gamma ferric oxide, $Fe_2O_3$ and magnetic ferrites; carbonyl iron is also suitable. These materials are in finely divided form with particle sizes generally between about 0.2 and 44 microns in maximum dimension. Carbonyl iron is typically utilized in spherical particle form, from about 1 to 5 microns in diameter. Magnetic particles are typically incorporated in the amount from 50% to 95% by weight.

The fluorescent pigments used in the inventive method consist of a fluorescent dye solvated in a thermoplastic resin, particularly, a cyclic aminotriazine resin, for example melamine-, or benzo-quanaminesulfonamide-formaldhyde resin. Fluorescent pigments of this type are available on the market under various proprietary names, for example, from the Day Glo Corporation, under the name "Day-Glo" fluorescent pigment. However, any fluorescent pigment can be used. Fluorescent pigments are typically incorporated in the amount from 5% to 50% by weight. Alternatively, although results are not as satisfactory, resins and fluorescent dyes can be separately mixed with a magnetic powder and the fluorescent dye caused to be solvated by the resins in situ.

In order to form the core particles, the magnetic and fluorescent pigment powders are suitably mixed in a blender or colloid mill under sufficiently high shear force to effect a cohesion between the magnetic and pigment particles due to the operation of Van der Wall forces. Preferably, the blade of the blender or rotor of the mill should be driven so as to rotate at a speed of at least 5400, up to 7500, or even 12,000, rpm. This causes the finely pigment particles to adhere directly to the magnetic particles.

Any organic substance which renders the encapsulating resin sufficiently tacky during the time of core-particle formation and does not unacceptably interfere with the desired properties of the core particles is suitable for use as a plasticizer. Typically, the plasticizer of the inventive method is a water immiscible, volatile solvent. Examples are naphtha and methylene chloride.

Any water-miscible solvent which exhibits properties consistent with attainment of the objects of the invention is suitable. Examples are solvents employed in conventional encapsulation methods. Typical water-miscible solvents are relatively volatile, oxygenated aliphatic organic solvents, such as the $C_1-C_5$ alcohols, for example methanol, ethanol (typically denatured), and propanol, isopropanol and butanol, as well as methylethyl ketone, acetone, and mixtures thereof. Solvents are typically incorporated in the amount from 15% to 31% by weight.

Any film-forming resin which effects an acceptable encapsulation and does not unsuitably interfere with the attainment of the objects of the invention is useful in practicing the invention. Resins are typically incorporated in the amount from 7% to 20% by weight. Examples are the resins employed in conventional encapsulation methods. A long chain linear polyamide is preferably employed as the film-forming resin. They are derived from the reaction of dimerized linoleic acid with diamines or other polyamines, of the general formula

$$HO(-OC-R-CONHR'-NH-)_nH$$

where R is hydrocarbon of up to 34 carbon atoms, $R^1$ is $-CH_2CH_2-$, and n is an interger of 2 or more. The polyamine generally used in the manufacture of a hard polyamide resin, which desirably has a melting point of over 100° C., is ethylene diamine. Blends of the polyamide resins having the desired melting point of 100° C. can be used. The preferred polyamide resins, which are of molecular weights averaging between 6,000 and 9,000, are thermoplastic, have sharp melting points between 105° and 115° C., and are soluble in the water-miscible aliphatic organic solvent utilized in the inventive method.

In accordance with the invention, either naphtha or another water-immiscible volatile solvent is incorporated as a plasticizer in a bath containing the core particles and aliphatic solvent. The plasticizer is incorporated in an amount sufficient to effect the desired encapsulation, typically 0.1 to 1.2% by weight. The other components are incorporated in conventional amounts. The solvent is preferably isopropanol. Since the naphtha or other plasticizer selected is not miscible with water, it is preferentially absorbed by the core particles. When the hot resin precipitates as a film, the naphtha, or other water immiscible solvent, acts as a plasticizer for the resin, prolonging its "tacky" condition. This allows for a more thorough encapsulation of the core particle. After filtration, the naphtha, or other plasticizer additive, evaporates during the drying process, along with the water and volatile water-miscible solvent, such as isopropanol, which is used.

Further objects of the invention, together with additional features contributing thereto and accruing therewith, will be apparent from the following examples of the invention.

EXAMPLE 1

The materials to be used are provided in the following amounts:

EXAMPLE 1

| | |
|---|---|
| "Day-Glo" fluorescent pigment; color:fire orange #GT-14N | 50.0 g. |
| Iron Powder | 50.0 g. |
| Isopropanol | 150.0 g. |
| Naphtha | 0.1 g. |
| Resin | 10.0 g. |
| Sodium Nitrite | 1.0 g. |
| Total Powder | 110.0 g. |

Following preparation of the core particles the selected film-forming polyamide is dissolved in a water-miscible volatile solvent such as isopropanol. This is done by heating. Magnetic and fluorescent pigment core particles, and isopropanol are then placed in a mixing tank. The dissolved resin is then introduced into the mixing tank. The bath is cooled from about 110° F. to about 70° to 75° F. A plasticizer such as naphtha and water are introduced into the tank to effect encapsulation and the tank contents are mixed. At this point a corrosion inhibitor, such as crystalline sodium nitrite which has been dissolved in water, may be added. The mixture is then allowed to settle and separate. The liquid is then decanted and the remaining powder dried. This is done under relatively low temperatures, such that the dried aggregates are not subjected to temperatures in excess of about 100° C. The resulting dried fluorescent magnetic particles contain less than 1% moisture, and are constituted by a core of the admixed magnetic fluorescent pigment particles with an adherent coating thereover of the selected film-forming The material obtained by the foregoing method can be used, without grinding, for use in nondestructive testing of work pieces for surface and near-surface dicontinuities. Depending of course upon the purposes for which the fluorescent magnetic material of the invention is intended, the particle sizes can be varied from a large size, such as between 25 to 75 microns maximum dimension, to a relatively small particle size, such as between 3 and 25 microns in maximum.

EXAMPLE 2

The materials are provided in the following amounts:

EXAMPLE 2

| | |
|---|---|
| "Day-Glo" fluorescent pigment; color:arc yellow #GT-16N | 30.0 g. |
| "Day-Glo" fluorescent pigment color. Saturn yellow #GT-17N | 40.0 g. |
| Iron Powder | 50.0 g. |
| Isopropanol | 170.0 g. |
| Naphtha | 0.2 g. |
| Resin | 15.0 g. |

-continued

| | |
|---|---|
| Sodium Nitrite | 1.0 g. |
| Total Powder | 135.0 g. |

Following preparation of the core particles, the polyamide resin is again dissolved in isopropanol, by heating. The magnetic and fluorescent powder particles, isopropanol and plasticizer such as naphtha are placed in a mixing tank. A corrosion inhibitor such as crystalline sodium nitrite which has been dissolved in water, may be added. Water is then introduced into the mixing tank. The contents of the bath need not be cooled. Following the introduction of the water, the dissolved resin is introduced into the mixing tank for encapsulation. The tank contents are then allowed to settle and separate. The liquid which separates is decanted, and the resulting powder is dried as described above.

In general, room temperatures are used in the mixing and precipitating steps of the methods discussed above, except as where otherwise specified.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. A method of making a fluorescent magnetic composition, which comprises:
   admixing magnetic powder with fluorescent pigment powder to effect formation of core particles comprising adherent magnetic and pigment powder,
   admixing the core particles with a volatile water-miscible solvent, a plasticizer, water and a water-precipitable film-forming resin, either the water or the film-forming resin being incorporated as the last of such components to effect precipitation of the resin as an adherent coating on the core particles, and their encapsulation.

2. A fluorescent magnetic composition produced by the method defined in claim 1.

3. A method as defined in claim 1, wherein said water-miscible solvent is an oxygenated aliphatic organic solvent.

4. A fluorescent magnetic composition produced by the method defined in claim 3.

5. A method as defined in claim 3, wherein the solvent is an alcohol of from 1 to 5 carbon atoms, methyl-lethyl ketone, acetone, or a mixture of at least two of the foregoing.

6. A method as defined in claim 1, wherein said water-miscible solvent is isopropanol.

7. A method as defined in claim 1, wherein the plasticizer is a volatile water-immiscible solvent.

8. A fluorescent magnetic composition produced by the method defined in claim 7.

9. A method as defined in claim 7, wherein the plasticizer is methylene chloride or naphtha.

10. A method as defined in claim 7, wherein said plasticizer is naphtha.

11. The method of making a fluorescent magnetic composition, which comprises:
    admixing magnetic powder with fluorescent pigment powder to effect formation of core particles comprising adherent magnetic and pigment powders, admixing the core particles with a volatile water-miscible solvent, a plasticizer and water and combining such aqueous admixture with a water-precipitable film-forming resin to effect precipitation of the resin as an adherent coating on the core particles, and their encapsulation.

12. A fluorescent magnetic composition produced by the method defined in claim 11.

13. The method of making a fluorescent magnetic composition, which comprises:

admixing magnetic powder with fluorescent pigment powder to effect formation of core particles comprising adherent magnetic and pigment powders, admixing the core particles with a volatile water-miscible solvent, a plasticizer and a water-precipitable film-forming resin, and adding water to the resinous admixture to effect precipitation of the resin as an adherent coating on the core particles, and their encapsulation.

14. A fluorescent magnetic composition produced by the method defined in claim 13.

* * * * *